United States Patent
Landkammer

(10) Patent No.: US 9,714,895 B2
(45) Date of Patent: Jul. 25, 2017

(54) APPARATUS FOR MONITORING PARTICLES

(75) Inventor: Jan Landkammer, Tampere (FI)

(73) Assignee: Pegasor Oy, Tampere (FI)

( * ) Notice: Subject to any disclaimer, the term of this patent is extended or adjusted under 35 U.S.C. 154(b) by 222 days.

(21) Appl. No.: 13/578,887

(22) PCT Filed: Feb. 24, 2011

(86) PCT No.: PCT/FI2011/000012
§ 371 (c)(1),
(2), (4) Date: Aug. 14, 2012

(87) PCT Pub. No.: WO2011/104426
PCT Pub. Date: Sep. 1, 2011

(65) Prior Publication Data
US 2012/0304738 A1    Dec. 6, 2012

(30) Foreign Application Priority Data
Feb. 25, 2010 (FI) .................. 20100090 U

(51) Int. Cl.
*G01N 15/06* (2006.01)
*G01N 27/407* (2006.01)
(Continued)

(52) U.S. Cl.
CPC ........ *G01N 15/0656* (2013.01); *F01N 13/008* (2013.01); *G01N 27/4077* (2013.01);
(Continued)

(58) Field of Classification Search
CPC ....... G01N 15/0656; G01N 2015/0046; G01N 27/4077; F01N 13/008
(Continued)

(56) References Cited

U.S. PATENT DOCUMENTS

| | | | |
|---|---|---|---|
| 4,456,883 A | 6/1984 | Bullis et al. | |
| 6,164,120 A * | 12/2000 | Friese | G01N 27/4078 204/424 |

(Continued)

FOREIGN PATENT DOCUMENTS

| | | |
|---|---|---|
| DE | 2445004 A1 | 4/1976 |
| DE | 19853841 A1 | 6/1999 |

(Continued)

OTHER PUBLICATIONS

International Search Report from corresponding international application No. PCT/FI2011/000012, mailing date May 19, 2011.

*Primary Examiner* — Hezron E Williams
*Assistant Examiner* — David Z Huang
(74) *Attorney, Agent, or Firm* — Marshall, Gerstein & Borun LLP

(57) ABSTRACT

A new apparatus for monitoring fine particle concentration in an exhaust system of a combustion engine has a part that extends into the exhaust system, and a housing that includes structure that attaches and seals the apparatus to the exhaust system through a single opening in a wall of the exhaust system. A gas inlet in the housing provides a measurement flow into a particle measurement sensor inside the housing. At least a fraction of the particles entering the particle measurement sensor are charged, and at least a fraction of the current carried by the charged particles are detected. A gas outlet in the housing carries the measurement flow away from the particle measurement sensor. The structure that attaches the apparatus to the exhaust system has one electrical connector that provides power to the sensor, and another electrical connector that transmits the electrical signal created by the sensor.

4 Claims, 1 Drawing Sheet

(51) Int. Cl.
*G01N 15/00* (2006.01)
*F01N 13/00* (2010.01)
*G01N 1/24* (2006.01)

(52) U.S. Cl.
CPC ............ *G01N 2001/244* (2013.01); *G01N 2015/0046* (2013.01)

(58) Field of Classification Search
USPC .......................................... 73/23.31, 23.33
See application file for complete search history.

(56) References Cited

U.S. PATENT DOCUMENTS

| | | | |
|---|---|---|---|
| 7,406,855 B2 * | 8/2008 | Tikkanen et al. ............ | 73/23.31 |
| 2008/0016946 A1 * | 1/2008 | Thanigachalam et al. .. | 73/31.05 |
| 2010/0158758 A1 * | 6/2010 | Gustin ............................ | 422/83 |
| 2011/0050243 A1 * | 3/2011 | Tikkanen ............. | G01N 1/2252 |
| | | | 324/464 |
| 2011/0232268 A1 * | 9/2011 | Nelson ............... | G01N 15/0656 |
| | | | 60/276 |
| 2012/0234172 A1 * | 9/2012 | Sugiyama .......... | G01N 15/0656 |
| | | | 96/26 |

FOREIGN PATENT DOCUMENTS

| | | |
|---|---|---|
| JP | 60100046 | 6/1985 |
| JP | 60123761 | 7/1985 |
| JP | 2006078267 A | 3/2006 |
| JP | 2007519899 | 7/2007 |
| JP | 2008096170 | 4/2008 |
| JP | 2010032488 | 2/2010 |
| WO | WO-2004113904 A1 | 12/2004 |
| WO | WO-2009109688 A1 | 9/2009 |

* cited by examiner

APPARATUS FOR MONITORING PARTICLES

CROSS-REFERENCE TO RELATED APPLICATIONS

This is a United States national stage of international patent application no. PCT/FI2011/000012 filed Feb. 24, 2011, which in turn claims the priority benefit of Finnish patent application no. FI U20100090 filed Feb. 25, 2010, the entire respective disclosures of which are incorporated herein by reference.

FIELD OF INVENTION

The present invention relates to an apparatus for monitoring particles and especially to an apparatus as defined in the preamble of independent claim 1.

DESCRIPTION OF THE STATE OF THE ART

Fine particles having diameter between 1 nm and 10 μm are formed in many combustion processes. For various reasons these fine particles are measured. The fine particle measurements may be conducted because of their potential health effects and also for monitoring operation of combustion processes, such as operation of combustion engines, especially diesel engines. The above reasons there is need for reliable fine particle measurement apparatus.

One prior art method and apparatus for measuring fine particles is described in document WO2009109688 A1. In this prior art method clean, essentially particle free, gas is supplied into the apparatus and directed as a main flow via an inlet chamber to an ejector provided inside the apparatus. The clean gas is further ionized before and during supplying it into the inlet chamber. The ionized clean gas may be preferably fed to the ejector at a sonic or close to sonic speed. The ionizing of the clean gas may be carried out for example using a corona charger. The inlet chamber is further provided with a sample inlet arranged in fluid communication with a channel or a space comprising aerosol having fine particles. The clean gas flow and the ejector together cause suction to the sample inlet such that a sample aerosol flow is formed from the duct or the space to the inlet chamber. The sample aerosol flow is thus provided as a side flow to the ejector. The ionized clean gas charges the particles. The charged particles may be further conducted back to the duct or space containing the aerosol. The fine particles of the aerosol sample are thus monitored by monitoring the electrical charge carried by the electrically charged particles. Free ions may removed further be removed using an ion trap. In addition to the above mentioned fine particles industrial processes and combustion processes form usually also particles having particle diameter greater than 1 μm, or greater than 2 μm, 3 μm, 5 μm or even greater. These coarse particles having particle diameter greater than 1 μm may be formed in small amounts in normal operation conditions, but especially in special operation conditions such as during start ups, shutdowns, malfunction conditions. The size distribution of the diesel engine exhaust particles generally shows three different modes: the nuclei mode consists of particles having a diameter of less than approximately 50 nm, the accumulation mode consists of particles having diameters between 50 nm and 1 μm and in the coarse mode the particle diameter is greater than 1 μm. A majority of the diesel engine exhaust particles is born after the exhaust gases escape from the exhaust pipe and these particles typically belong to the accumulation and nuclei mode.

One important demand for the fine particle monitoring apparatuses especially for on-board-diagnoses of diesel engines is small and compact construction. Furthermore, it is also preferable that these fine particle monitoring apparatuses may be operated long time periods without need for maintenance. In many applications, such as monitoring fine particles of combustion engines, it is further preferable that the monitoring apparatus may be operated continuously for conducting fine particle measurements in real-time. Certain apparatuses used for diesel engine emission measurements are not sufficiently robust to withstand forces or temperatures encountered by such apparatuses and certain apparatuses cannot accurately indicate the presence of particulate matter due to poor signal noise ratio. Accordingly, in view of the shortcomings of apparatuses of the prior art, there is a need for improved apparatuses for monitoring fine particles flowing within an exhaust gas stream.

SUMMARY OF THE INVENTION

The object of the present invention is to provide an apparatus so as to overcome the prior art disadvantages. The objects of the present invention are achieved with an apparatus according to the characterizing portion of claim 1. The preferred embodiments of the invention are disclosed in the dependent claims.

The apparatus of one embodiment of the present invention has following specifications:
  volumetric flow of the essentially clean air: 0.5-5 dm$^3$/min at NTP
  measurement flow from the exhaust system: 1-10 dm$^3$/min at NTP
  assembly thread: M29×1.5
  impact resistance: >30G
  operational range (for exhaust gas particle concentration): <25 mg/m$^3$

BRIEF DESCRIPTION OF THE DRAWINGS

In the following, the invention will be described in more detail with reference to the appended principle drawing, in which.

DETAILED DESCRIPTION OF PREFERRED EMBODIMENTS

Figure 1:
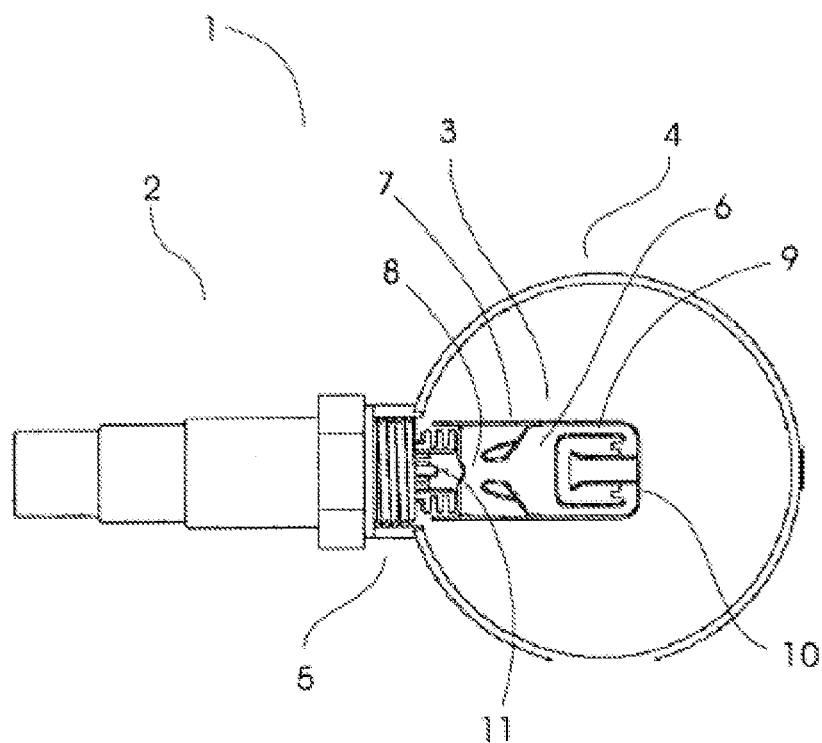
FIG. 1 shows an embodiment of the invented apparatus.
For the sake of clarity, the figures only show the details necessary for understanding the invention. The structures and details which are not necessary for understanding the invention and which are obvious for a person skilled in the art have been omitted from the figures in order to emphasize the characteristics of the invention.
Figure 2:
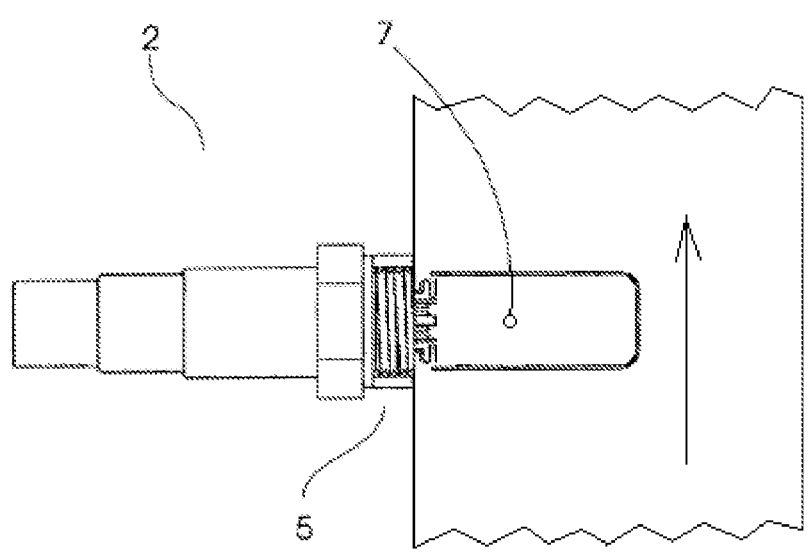
FIG. 2 is a side view of the apparatus.

Apparatus 1 comprises a housing including part 3 extending into the exhaust system 4 of a combustion engine. The apparatus 1 has an attachment means 5 that is attached and sealed to the wall of the exhaust system 4, preferably to the wall of an exhaust pipe of a combustion engine. Here, as seen in FIG. 1, the attachment means takes the form of a stem that encloses a pair of electrical connectors 21 and 22 and a gas connector 23. A particle measurement sensor 6 is placed inside the housing 2 and the housing 2 has an inlet hole 7 for providing a measurement flow to the sensor 6 and an outlet hole 10 for exiting the measurement flow. The apparatus also has means 8 for charging at least a fraction of the particles entering the sensor 6, and means for measuring the electrical current carried by the charged particles. It is essential to the present invention that assembling the apparatus to the exhaust pipe only requires a single opening in the pipe and thus easy and non-expensive assembly is achieved. The coupling to the single opening in the exhaust pipe comprises an electrical coupling for providing power to the sensor, such as high voltage to a means 11 for ionizing essentially clean air, such as a corona discharge device used to ionize the essentially clean gas flow, another electrical coupling for transmitting the electrical signal generated by the particle measurement sensor and a gas coupling for providing essentially clean air to the sensor. These couplings are placed in the means 5 for attaching apparatus 1 to the exhaust system 4. The sensor preferably includes a venturi throat and particle ionizing chamber such as described in WO2009109688 A1.

The length of part 1 extending into the exhaust gas system is preferably less than or equal to 55 mm. The length of the part of apparatus 1 expanding outside the exhaust gas system wall is preferably 30-50 mm. Part 1 is preferably assembled into the exhaust gas system in such direction that the gas flowing in the exhaust pipe does not directly enter to the inlet hole in the housing. Although this is in contradiction to the isokinetic particle sampling well known to a person skilled in the art, it provides a beneficial effect as coarse particles in the exhaust gas flow tend not to enter the inlet hole. In one embodiment of the present invention the inlet hole is placed such that the housing wall effectively shadows the inlet hole and there is no line-of-sight route of particles into the inlet hole. This is especially a beneficial embodiment when the particle sensor comprises an essentially clean gas flow, such as described in WO2009109688 A1, which provides a pressure difference between the inlet hole and the exhaust pipe such that the pressure at the inlet hole is lower than the pressure in the exhaust pipe.

The embodiment of FIG. 1 shows a structure where the part 1 extending into the exhaust system comprises parts manufactured from sheet metal. In the preferred embodiment of the invention the essential parts of part 1 extending into the exhaust system are manufactured from sheet metal which provides a structure which can be easily manufactured and is non-expensive. Especially the part of housing 1 inside the exhaust system, venturi throat and ion trap 9 are manufactured from sheet metal in the preferred embodiment of the invention.

It is possible to produce various embodiments of the invention in accordance with the spirit of the invention. Therefore, the above-presented examples must not be interpreted as restrictive to the invention, but the embodiments of the invention can be freely varied within the scope of the inventive features presented in the claims herein below.

The invention claimed is:

1. An apparatus for monitoring fine particle concentration in a flow of exhaust in a flowpath in a duct of an exhaust system of a combustion engine, comprising:
    a) a stem that attaches and seals the apparatus to the exhaust system through a single opening in a wall of the exhaust system;
    b) an inside part that has a single-walled housing and is arranged to be installed inside the duct of the exhaust system through the single opening in the wall of the exhaust system in an arrangement in which the entirety of the single-walled housing directly faces the flowpath in the duct;
    c) a particle measurement sensor that is inside the single-walled housing of the inside part;
    d) a gas inlet that is on the single-walled housing of the inside part, provides at least a part of a measurement flow to the particle measurement sensor, and is positioned within the duct such that there is no direct line-of-sight route for particles flowing through the duct to enter the single-walled housing;
    e) a corona discharge device that is inside the single-walled housing of the inside part and ionizes essentially clean gas and separately provides essentially clean ionized gas to the particle measurement sensor, the clean ionized gas charging at least a fraction of the particles in the measurement flow; and
    f) a gas outlet that is on the single-walled housing of the inside part, through which the measurement flow exits the single-walled housing after passing the particle measurement sensor; and
    g) an outside part that is arranged to extend from the single opening of the wall of the exhaust system outside the wall of the exhaust system.

2. An apparatus according to the claim 1, wherein the single-walled housing of the inside part comprises parts manufactured from sheet metal.

3. An apparatus according to claim 1, wherein the length of the single-walled housing of the inside part is less than or equal to 55 mm in length.

4. An apparatus for monitoring the concentration of fine particles in a flowpath of a flow of exhaust in a duct of an exhaust system of a combustion engine, comprising:
    a single stem that forms a sole projection of the apparatus into the duct of the exhaust system, and encloses a pair of electrical connectors and a gas connector;
    an inside part of the apparatus that has a single-walled housing and is arranged to extend from the stem into a gas flowpath within the duct in an arrangement in which the entirety of the single-walled housing directly faces the flowpath in the duct;
    a gas inlet that is on the single-walled housing of the inside part of the apparatus, draws a measurement flow from the gas flowpath in the exhaust system into the single-walled housing of the inside part of the apparatus, and is positioned within the duct such that there is no direct line-of-sight route for particles flowing through the duct to enter the single-walled housing;
    an ionizer that is mounted within the single-walled housing of the inside part of the apparatus and ionizes essentially clean gas from the gas connector, the ionized gas then being combined with the measurement flow, and electrically charging particles in the measurement flow;
    a particle measurement sensor that is mounted within the single-walled housing of the inside part of the apparatus, is powered by electricity from one of the electrical connectors, senses the charge of particles in the measurement flow, and delivers a charge signal along the other of the electrical connectors;
    a gas outlet that is on the single-walled housing of the inside part of the apparatus, through which the measurement flow exits the single-walled housing of the inside part of the apparatus after passing the particle measurement sensor.

* * * * *

UNITED STATES PATENT AND TRADEMARK OFFICE
CERTIFICATE OF CORRECTION

PATENT NO. : 9,714,895 B2
APPLICATION NO. : 13/578887
DATED : July 25, 2017
INVENTOR(S) : Jan Landkammer It is certified that error appears in the above-identified patent and that said Letters Patent is hereby corrected as shown below:

In the Claims

At Column 4, Line 53, "flow, and" should be -- flow, --.

Signed and Sealed this
Twentieth Day of March, 2018

Andrei Iancu
*Director of the United States Patent and Trademark Office*